United States Patent [19]

Larock

[11] Patent Number: 5,164,518

[45] Date of Patent: Nov. 17, 1992

[54] PALLADIUM-CATALYZED COUPLING OF ARYL HALIDES, NON-CONJUGATED DIENES AND CARBON NUCLEOPHILES

[75] Inventor: Richard C. Larock, Ames, Iowa

[73] Assignee: Iowa State University Research Fondation Inc., Ames, Iowa

[21] Appl. No.: 729,428

[22] Filed: Jul. 12, 1991

[51] Int. Cl.$^5$ .......................................... C07D 317/50
[52] U.S. Cl. .................................. 549/447; 546/341; 549/79; 549/80; 549/318; 549/434; 549/347; 549/367; 549/374; 560/61; 560/100; 560/104; 560/102; 558/406; 568/28; 568/376
[58] Field of Search ............... 560/100, 104, 61, 102; 558/406; 568/376, 28; 549/318, 79, 80, 499, 500, 497, 434, 374, 369, 347; 546/341

[56] References Cited

U.S. PATENT DOCUMENTS

| | | | |
|---|---|---|---|
| 3,454,538 | 7/1969 | Naarmann et al. | 560/243 |
| 3,479,379 | 11/1969 | Ketley | 556/136 |
| 3,479,392 | 11/1969 | Stern et al. | 526/171 |
| 3,527,794 | 9/1970 | Heck | 560/104 |
| 3,584,020 | 6/1971 | Bach | 556/136 |
| 3,642,902 | 2/1972 | Bach et al. | 556/136 |
| 3,700,727 | 10/1972 | Heck | 560/104 |
| 3,998,872 | 12/1976 | Symon et al. | 560/174 |
| 4,065,479 | 12/1977 | Larock | 556/136 |
| 4,335,054 | 6/1982 | Blaser et al. | 560/10 |
| 4,632,996 | 12/1986 | Larock et al. | 556/135 |

FOREIGN PATENT DOCUMENTS 0132527 11/1967 Japan .

OTHER PUBLICATIONS

A. C. Albeniz et al., *J. Am. Chem. Soc.*, 112, 6594 (1990).
G. Albelo et al., *J. Am. Chem. Soc.*, 97, 16 (1975).
B. Akermark et al., *J. Org. Chem.*, 54, 1110 (1989).
D. D. Bender et al., *J. Org. Chem.*, 47, 1278 (1982).
S. S. Hall et al., *Organometallics*, 3, 1745 (1984).
R. C. Larock et al., *Tetrahedron Letters*, 24, 3457 (1983).
R. C. Larock et al., *J. Org. Chem.*, 49, 2701 (1984).
R. C. Larock et al., *J. Chem. Soc., Chem. Commun.*, 834 (1987).
R. C. Larock et al., *Tetrahedron Letters*, 28, 5291 (1987).
R. C. Larock et al., *Tetrahedron Letters*, 29, 6399 (1988).
R. C. Larock et al., *J. Org. Chem.*, 53, 4329 (1988).
R. C. Larock et al., *Tetrahedron Lett.*, 30, 6629 (1989).
R. C. Larock et al., *J. Org. Chem.*, 55, 6244 (1990).
R. C. Larock et al., *J. Org. Chem.*, 55, 407 (1990).
s. A. Lebedev et al., *Metal. Org. Chem.*, 2, 624 (1989) (*Chem. Abstracts*, 111:231969z (1989)).
J. M. O'Connor et al., *J. Org. Chem.*, 48, 807 (1983).
B. C. Soderberg et al., *J. Org. Chem.*, 53, 2925 (1988).
B. C. Soderberg et al., *J. Org. Chem.*, 55, 1344 (1990).
M. Uno et al., *J. Chem. Soc., Chem. Commun.*, 785 (1987).
M. Uno et al., *J. Chem. Soc. Perkin Trans.*, 1, 647 (1990).

*Primary Examiner*—Richard L. Raymond
*Assistant Examiner*—Mark W. Russell

[57] ABSTRACT

The present invention provides a method for the alpha,omega-arylation/alkylation of a non-conjugated diene in one step by reacting the diene with an aryl iodide or an aryl bromide and a carbon nucleophile in the presence of an amount of a Pd(O) complex effective to catalyze the reaction.

27 Claims, No Drawings

PALLADIUM-CATALYZED COUPLING OF ARYL HALIDES, NON-CONJUGATED DIENES AND CARBON NUCLEOPHILES

BACKGROUND OF THE INVENTION

This invention was made with the support of NIH Grant No. GM 24254. The U.S. Government has certain rights in this invention.

Synthetic methodology which allows for a rapid increase in molecular complexity is extremely valuable in organic chemistry, particularly when it generates more than one new carbon-carbon bond at a time, accommodates considerable functionality and is broad in scope. Recently carbon-carbon bond formation catalyzed by transition-metal complexes has been used extensively in organic syntheses. In such reactions, $\pi$-allylmetal complexes frequently play an important role because of their high reactivities toward various nucleophiles, which result in transfer of the allyl groups from the metal to the nucleophiles. See, F. R. Hartley et al., eds., *The Chemistry of the Metal-Carbon Bond*, Vol. 4, John Wiley and Sons, N.Y. (1987). For example, M. Uno et al., *J. Chem. Soc. Perkin Trans.*, 1, 647 (1990), reported that a palladium-phosphine complex catalyzes the 1,4-arylation/alkylation reaction of buta-1,3-diene with halogenoarenes and stabilized anions such as $-CH(CN)_2$, $-CH(CN)CO_2Me$, and $-CH(CO_2Et)_2$, where two carbon-carbon bonds are built up from three components by a tandem insertion/coupling reaction in one catalytic cycle. This reaction is summarized in Scheme I, below.

Scheme I

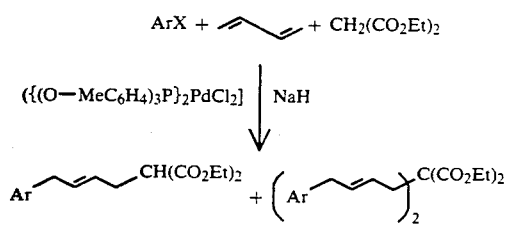

wherein Ar is, e.g., phenyl and X is halogen.

S. A. Lebedev et al., in *Mettaloorg. Khim.*, 2, 624 (1989) (Chem. Abstr., 111, 231969z (1989), reported that $(PhCN)_2PdCl_2$ catalyzed the 1,4-addition of $Me_3SnPh$ to 1,3-butadiene to yield $PhCH_2CH=CHCH_2Ph$.

J. M. O'Connor et al., in *J. Org. Chem.*, 48, 807 (1983) reported the reaction of 1-bromo-2-methylpropene and sodium diethylmalonate with the conjugated diene isoprene in the presence of $Pd(OAc)_2 \cdot 2Ph_3P$ to yield 22% of dimethyl(2,6-dimethyl-hepta-2,5-dien-1-yl)malonate. Also, D. O. Bender et al., in *J. Org. Chem.*, 47, 1278 (1984) reported the coupling of an aryl halide, a 1,4-diene and a secondary amine in the presence of palladium acetate-tri-o-tolylphosphine, to form mixtures of phenyl pentadienes and phenylpentenylamines, each in less than 50% yield.

However, a need exists for simple synthetic methods to accomplish the alpha,omeqa-aryl/alkylation of non-conjugated alkenes in high yields.

SUMMARY OF THE INVENTION

The present invention provides a synthetic method for the alpha,omeqa-arylation/alkylation of a non-conjugated diene, comprising reacting a compound of the formula ArI or ArBr, wherein Ar is a substituted or unsubstituted aryl moiety, with a non-conjugated acyclic or cyclic diene and a carbon nucleophile of the general formula $HC(X)(Y)(Z)$, wherein X is preferably H, $(C_1-C_4)$alkyl, Ar or $Ar(C_1-C_4)$alkyl; and Y and Z are individually CN, $CO_2-(C_1-C_4)$alkyl, $(C_1-C_4)$alkylcarbonyl, $-SO_2Ar$ or taken together $-C(O)(CH_2)_m-C(O)-$ wherein m is about 3–6 or $-CO_2-(CH_2)_n-$ wherein n is about 2–6, in the presence of an effective amount of a Pd(O) catalyst and a base to yield a compound of the formula I:

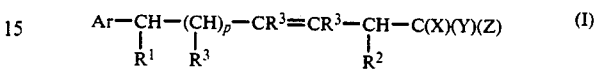

wherein p is at least 1, and $R^1$ and $R^2$ are individually H, $(C_1-C_8)$alkyl, Ar, $Ar(C_1-C_4)$alkyl, or taken together are $-(CH_2)_q-$; q is at least 1, preferably 1–3; wherein each $R^3$ is H, $(C_1-C_8)$alkyl, Ar or $Ar(C_1-C_4)$alkyl; and wherein Ar, X, Y, and Z are as described above.

The diene component of the present invention can be represented by the formula (II):

wherein $R^1$, $R^2$, $R^3$ and p are as defined above. Preferably, p is 1–2 to about 9–10 and q is 1 to about 10. Preferably, each $R^3$ is H or $(C_1-C_8)$alkyl, most preferably each $R^3$ is H or $CH_3$. In fact, the upper limits of both p and q are controlled only by physical or practical considerations, such as solubility of the starting material and the product cost of the starting material, reaction conditions and the like.

The compounds of formula I are apparently formed by arylpalladium generation and addition to the less substituted end of the diene, palladium migration down the carbon chain to form a $\pi$-allylpalladium intermediate, and carbanion displacement of the palladium moiety.

The compounds of formula I can be utilized directly, e.g., as substituted unsaturated monomers for the preparation of aralkyl-substituted polymers, or can be utilized indirectly as intermediates in the synthesis of more complex bioactive compounds. Cleavage of the double bond in compounds of formula I can yield arylalkanoic acids.

DETAILED DESCRIPTION OF THE INVENTION

A wide variety of substituted and unsubstituted aryl iodides or aryl bromides (ArI or ArBr) can be employed in the present process, and the Ar("aryl") substituent(s) on the diene or on the carbon nucleophile can likewise be substituted or unsubstituted. Preferably, Ar is a $C_6$–$C_{10}$ aryl moiety, such as phenyl, naphthyl, 2- or 3-thienyl, 2-or 3-furyl, 2-, 3- or 4-pyridyl and the like. A wide variety of 1–3 non-iodo substituents can be present on the aryl ring, including Cl, Ar, Br, F, formyl, amino, nitro, $-CH(OCH_3)_2$, $-CH(OEt)_2$, $-CO_2R^3$, $-CN$, $(C_1-C_4)$alkyl, $(C_1-C_4)$-alkoxy, ArO—, 3,4-methylenedioxy, $(C_1-C_4)$alkoxycarbonyl, $(C_1-C_4)$alkylcarbonyl, $(R^4)(R^5)N$, $(R^5)S$—, wherein $R^4$ and $R_5$ are each $(C_1-C_4)$alkyl, phenyl or mixtures thereof. Other representative Ar-substituents are given in Blaser et al. (U.S. Pat. No. 4,335,054), the disclosure of which is incorporated by reference herein, at Col. 2, line 19 to Col. 3, line 3. If an aryl bromide is used, the substituents are preferably electron-withdrawing. As used throughout, the term "alkyl" includes branched or straight-chain alkyl. Preferably Ar is phenyl, tolyl, xyxyl, anisyl or 3,4-methylene-dioxy.

The palladium(O) (Pd(O)) catalyst is generally employed in an amount of about 0.001-20 mol-%, preferably 0.001-3 mol-%, based on the aryl halide. Useful catalysts include Pd(O) complexes such as bis-(dibenzylidene-acetone)-palladium(O), bis-(isonitrile)-palladium(O), bis-(cyclohexylisonitrile)-palladium(O), bis-(isopropylisonitrile)-palladium(O), bis-(tert.-butylisonitrile)-palladium(O), bis-(p-tolylisonitrile)-palladium(O), bis-(phenylisonitrile)-palladium(O), and bis-(p-methoxyphenylisonitrile)-palladium(O). Amongst the above compounds, bis-(dibenzylidene-acetone)-palladium(O) is preferred.

Other catalysts, e.g., Pd(II) catalysts, can also be used in the present method, which yield Pd(O) during the course of the reaction. These include $PdCl_2$, $Pd(OAc)_2$, $PdBr_2$, $Pd(CN)_2$, $Pd(NO_3)_2$ and the like. Other Pd catalysts which can be used in the present method include those disclosed in Blaser et al. (U.S. Pat. No. 4,335,054) at Col. 6, line 5 to Col. 7, line 3.

Bases used in the present process can be inorganic or organic bases, which are adequately soluble in the reaction medium. Representative bases are disclosed at Col. 7, lines 8-65 of the Blaser et al. patent. Preferred inorganic bases for use in the present process include $Na_2CO_3$, $KHCO_3$, $K_2CO_3$, $Li_2CO_3$, and the most preferred inorganic base $NaHCO_3$. The preferred organic bases are trialkylamines.

A source of halide, preferably of chloride ($Cl^-$), is also preferably employed in the present process, and can act to increase both the reaction rates and the yields. Preferred chloride sources are tetralkyl- or tetraaryl ammonium chlorides, tetraalkyl or tetraaryl phosphonium chlorides and alkali metal chlorides, including tetra-n-butylammonium chloride (n-Bu$_4$NCl) and lithium chloride.

In carrying out the synthesis of the compounds of formula I, the aryl iodide or aryl bromide, the diene (II) and the carbon nucleophile, HC(X)(Y)(Z), are combined in a mole ratio of about 1:1-10:1-10; preferably, about 1:2-5:2-5 in a suitable organic solvent with the Pd(O) catalyst, the base, and preferably, the chloride source, and the reaction mixture is heated at about 60°-120° C. for about 5-50 hours under an inert atmosphere, i.e., until the ArI or ArBr is consumed. The crude product I is extracted, i.e., into diethyl ether and can be purified by chromatography.

Preferred organic solvents are those which are polar. These include ($C_1$-$C_4$)alkanols, tetrahydrofuran (THF), acetonitrile, ethers, glycol ethers, dimethylformamide, hexamethylphosphoramide and dimethylsulfoxide.

The invention will be further described by reference to Examples 1-21, as summarized on Table I, below. These examples were carried out using the following experimental procedure.

EXAMPLE 1

To a culture tube (16×125 mm) with a micromagnetic stirring bar was added sodium bicarbonate (0.105 g, 1.25 mmol), tetra-n-butylammonium chloride (0.153 g, 0.55 mmol) and bis(dibenzylideneacetone)palladium(O) (0.014 g, 0.025 mmol). After flushing with nitrogen gas for several minutes, 1 or 2 ml of dimethyl sulfoxide was injected into the tube through a septum. Then the aryl halide (0.50 mmol) was added, followed by the non-conjugated diene (1.00 or 2.50 mmol) and the carbon nucleophile (1.00 or 2.50 mmol). After the addition of all reagents, the culture tube was sealed with a screw cap lined with Teflon and the reaction mixture was stirred at 80° C. for the reaction time indicated in Table I. The reaction mixture was allowed to cool to room temperature, diluted with ethyl ether (10 ml) and washed three times (20 ml×3) with saturated aqueous ammonium chloride. The aqueous layer was back-washed twice (20 ml×2) with ether. The combined ether layer was dried over anhydrous $Na_2SO_4$ and evaporated under reduced pressure to remove the solvent. Finally, the product was isolated by flash chromatography on a silica gel column. All coupling products were characterized by $^1H$ and $^{13}C$ NMR, FT-IR, and mass spectrometry or elemental analysis.

TABLE I
Palladium-Catalyzed Coupling of Aryl Iodides, Non-Conjugated Dienes and Carbon Nucleophiles

| Ex. | aryl iodide | diene | equivs | carbon nucleophile | equivs | time (h) | product | % isolated yield |
|---|---|---|---|---|---|---|---|---|
| 1 | $C_6H_5I$ | $H_2C=CH(CH_2)_2CH=CH_2$ | 1 | $H_2C(CO_2C_2H_5)_2$ | 1 | 24 | $E-C_6H_5(CH_2)_3CH=CHCH_2CH(CO_2C_2H_5)_2$ | 29 |
| 2 | | | 1 | | 2 | 24 | | 68 |
| 3 | | | 2 | | 1 | 48 | | 65 |
| 4 | | | 2 | | 2 | 12 | | 82 |
| 5 | | | 2 | | 5 | 12 | | 76 |
| 6 | | | 5 | | 2 | 12 | | 62 |
| 7 | | | 5 | | 5 | 12 | | 82 |
| 8 | | | 2 | $NCCH_2CO_2C_2H_5$ | 2 | 12 | $E-C_6H_5(CH_2)_3CH=CHCH_2CH(CN)CO_2C_2H_5$ | 32 |
| 9 | | | 5 | | 5 | 12 | | 81 |
| 10 | | | 2 | ![2-methyl-1,3-cyclohexanedione] | 2 | 12 | $E-C_6H_5(CH_2)_3CH=CHCH_2-$ (2-methyl-1,3-dioxocyclohexyl) | 72 |
| 11 | | | 5 | ![3-acetyl-γ-butyrolactone] | 5 | 12 | $E-C_6H_5(CH_2)_3CH=CHCH_2-$ (3-acetyl-γ-butyrolactonyl) | 64 |
| 12 | | | 5 | | 5 | 12 | | 64 |
| 13 | | $H_2C=CH(CH_2)_4CH=CH_2$ | 5 | $H_2C(CO_2C_2H_5)_2$ | 5 | 12 | $E-C_6H_5(CH_2)_5CH=CHCH_2CH(CO_2C_2H_5)_2$ | 66 |
| 14 | | $H_2C=CH(CH_2)_{10}CH=CH_2$ | 2 | | 2 | 24 | $E-C_6H_5(CH_2)_{11}CH=CHCH_2CH(CO_2C_2H_5)_2$ | 52 |
| 15 | | $H_2C=CH(CH_2)_2C(CH_3)=CH_2$ | 5 | | 5 | 36 | $E-C_6H_5(CH_2)_3CH=C(CH_3)CH_2CH(CO_2C_2H_5)_2$ | 60 |
| 16 | | (1,3-cyclohexadiene) | 2 | | 2 | 12 | (trans-4-phenyl-3-cyclohexenyl)-$CH(CO_2C_2H_5)_2$ | 84 |
| 17 | $p-CH_3OC_6H_4I$ | $H_2C=CH(CH_2)_2CH=CH_2$ | 5 | | 5 | 12 | $E-p-CH_3OC_6H_4(CH_2)_3CH=CHCH_2CH(CO_2C_2H_5)_2$ | 88 |
| 18 | $p-CH_3COC_6H_4I$ | | 5 | | 5 | 12 | $E-p-CH_3COC_6H_4(CH_2)_3CH=CHCH_2CH(CO_2C_2H_5)_2$ | 54 |
| 19 | | | 5 | | 5 | 8 | | 56 |
| 20 | 2-iodothiophene | | 2 | | 2 | 12 | E-(2-thienyl)$(CH_2)_3CH=CHCH_2CH(CO_2C_2H_5)_2$ | 55 |
| 21 | | | 5 | | 5 | 12 | | 59 |

This process is surprisingly versatile, giving good yields for a variety of carbon nucleophiles. It works well for acyclic or cyclic dienes with anywhere from 1 to 10 carbons between the carbon-carbon double bonds (Examples 13-17), and accommodates electron-rich (Example 18) or electron-poor (Example 19) aryl halides, as well as heterocyclic halides (Examples 20 and 21).

Only products arising from regioselective syn insertion of the less substituted double bond are observed (Example 15). Careful spectroscopic examination of the products provides no evidence of aryl addition to the internal carbon of the carbon-carbon double bond of the diene as sometimes observed in related reactions. (R. C. Larock et al., *Tetrahedron Lett.*, 30, 6629 (1989); R. C. Larock et al., *J. Org. Chem.*, 55, 6244 (1990)).

These reactions presumably proceed by oxidative addition of the aryl halide to Pd(O), arylpalladium addition to one of the carbon-carbon double bonds, palladium migration to form a π-allylpalladium intermediate, and carbanion displacement of the palladium moiety as illustrated in Scheme II.

Scheme II

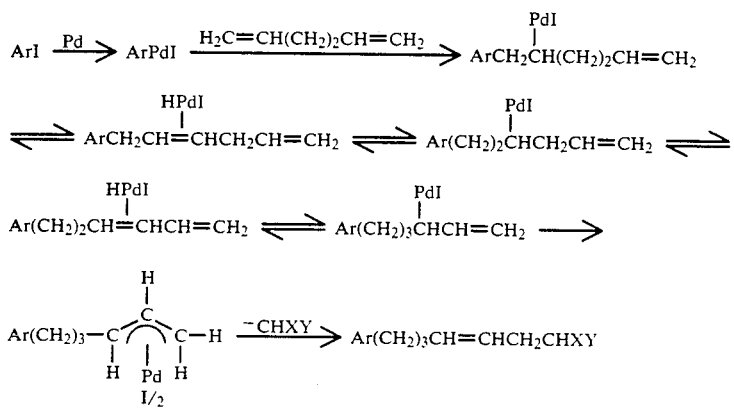

Fortunately, only minor amounts of aryl diene or $CH_3CH_2(CH_2)_pCH=CHCH_2CHXY$ side products are observed under these reaction conditions, even though the present reaction is run in the presence of base, carbanions and a very polar solvent, any of which might have been expected to displace a palladium hydride from any of the intermediate palladium hydride diene π-complexes. It is indeed noteworthy that in the present process, palladium can apparently reversibly migrate up and down even very long carbon chains without noticeable formation of aryl dienes or any significant decrease in the yield of the coupled product.

As shown in Scheme II, this migration process is believed to proceed by a series of reversible palladium hydride syn eliminations and readditions as judged by the exclusive formation of the trans product from 1,4-cyclohexadiene (Examples 16 and 17). The backside displacement of palladium from π-allylpalladium compounds by stabilized carbanions generated from the β-dicarbonyl compounds and the α-cyano ester by proton abstraction by the weak base sodium bicarbonate results in the observed product. Only products of carbanion attack at the remote end of the carbon chain are observed. All products consist exclusively of the E isomers shown in the Table, even when a trisubstituted double bond is formed (Example 15).

The invention has been described with reference to various specific and preferred embodiments and techniques. However, it should be understood that many variations and modifications may be made while remaining within the spirit and scope of the invention.

What is claimed is:

1. A method for the α,ω-arylation/alkylation of a non-conjugated diene comprising reacting (i) a compound of the formula ArI or ArBr, wherein Ar is substituted or unsubstituted aryl, with a (ii) non-conjugated acyclic diene or a non-conjugated cyclic diene of the formula:

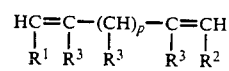

wherein $R^1$ and $R^2$ are each H, $(C_1-C_8)$alkyl, Ar, Ar($C_1-C_4$)alkyl, or, taken together, are $—(CH_2)_q—$ wherein q is at least 1; each $R^3$ is H, $(C_1-C_8)$alkyl, Ar, or Ar($C_1-C_4$)alkyl; and p is at least 1; and (iii) a carbon nucleophile of the general formula HC(X)(Y)(Z), wherein X is H, $(C_1-C_4)$alkyl, Ar or Ar($C_1-C_4$)alkyl; and Y and Z are individually CN, $(C_1-C_4)$alkylcarbonyl, $CO_2—(C_1-C_4)$alkyl, $SO_2Ar$ or, taken together, are $—C(O)(CH_2)_m—C(O)—$, wherein m is about 3-6, or $—CO_2—(CH_2)_n—$, wherein n is about 2-6; in the presence of (iv) an effective amount of a Pd(O) catalyst and (v) a base, to yield a compound of the formula:

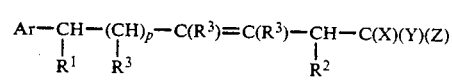

wherein p is at least 1, $R^1$ and $R^2$ are individually H, $(C_1-C_8)$alkyl, Ar, Ar($C_1-C_4$)alkyl, or taken together are $—(CH_2)_q—$, wherein q is at least 1; wherein each $R^3$ is H, $(C_1-C_8)$alkyl, Ar or Ar($C_1-C_4$)alkyl and wherein Ar, X, Y and Z are as described above.

2. The method of claim 1 wherein $R^1$ and $R^2$ are individually H or $(C_1-C_8)$alkyl.

3. The method of claim 1 wherein each $R^3$ is H or $CH_3$.

4. The method of claim 2 wherein p is 1-10.

5. The method of claim 1 wherein $R^1$ and $R^2$ are $—(CH_2)_q—$, q is 1-10, and p is 1-10.

6. The method of claim 1 wherein X is H.

7. The method of claim 6 wherein Y and Z are each CN or $CO_2(C_1-C_4)$alkyl.

8. The method of claim 1 wherein the Pd(O) catalyst is bis(dibenzylidene-acetone)Pd(O).

9. The method of claim 1 wherein the base comprises a bicarbonate salt.

10. The method of claim 1 wherein the reaction is carried out at about 60°-120° C. for about 5-50 hours.

11. The method of claim 1 wherein the reaction is carried out in dimethylsulfoxide solution.

12. The method of claim 1 where the mole ratio of (i):(ii):(iii) is about 1:1-10:1-10.

13. The method of claim 1 wherein Ar is phenyl.

14. The method of claim 1 wherein the reaction is carried out in the presence of a chloride source.

15. The method of claim 14 wherein the chloride source is (n-Bu)$_4$NCl.

16. A method for the α,ω-arylation/alkylation of a nonconjugated diene comprising reacting (i) a compound of the formula ArI, wherein Ar is substituted or unsubstituted phenyl, with (ii) a diene of the formula:

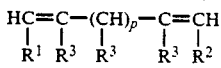

wherein $R^1$ and $R_2$ are each H, $(C_1-C_8)$alkyl, Ar, Ar($C_1-C_4$)alkyl, or, taken together, are —(CH$_2$)$_q$—, wherein q is at least 1; each $R^3$ is H, $(C_1-C_8)$alkyl, Ar or Ar($C_1-C_4$)alkyl; and p is 1-10; and (iii) a carbon nucleophile of the general formula HC(X)(Y)(Z), wherein X is H, $(C_1-C_4)$alkyl, phenyl or phen($C_1-C_4$)alkyl; and Y and Z are individually CN, $(C_1-C_4)$alkylcarbonyl, CO$_2$—$(C_1-C_4)$alkyl or, taken together, are —C(O)(CH$_2$)$_m$—C(O)—, wherein m is about 3-6, or —CO$_2$—(CH$_2$)$_n$—, wherein n is about 2-6; in the presence of (iv) an effective amount of a Pd(O) catalyst (v) a base, and (vi) a chloride source, to yield a compound of the formula:

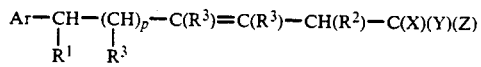

wherein Ar, $R^1$, p, $R^2$, $R^3$, X, Y and Z are as defined above.

17. The method of claim 16 wherein Ar is phenyl, tolyl, anisyl or 3,4-methylenedioxyphenyl.

18. The method of claim 16 wherein $R^1$ and $R^2$ are H.

19. The method of claim 16 wherein X is H.

20. The method of claim 16 wherein each $R^3$ is H or CH$_3$.

21. The method of claim 16 wherein Y and Z are both CN or CO$_2$CH$_3$.

22. The method of claim 16 wherein p is 1-10.

23. The method of claim 1 wherein p is 1-10 and $R^1$ and $R^2$ are —(CH$_2$)$_q$— wherein q is about 1-10.

24. The method of claim 16 wherein the mole ratio of (i):(ii):(iii) is about 1:1-2.5:1-2.5.

25. The method of claim 16 wherein the base comprises an inorganic base.

26. The method of claim 25 wherein the base comprises NaHCO$_3$.

27. The method of claim 25 wherein the chloride source is tetra-n-butylammonium chloride.

* * * * *

UNITED STATES PATENT AND TRADEMARK OFFICE
CERTIFICATE OF CORRECTION

PATENT NO. : 5,164,518

DATED : November 17, 1992

INVENTOR(S) : Larock

It is certified that error appears in the above-identified patent and that said Letters Patent is hereby corrected as shown below:

On the title page, item (73) Assignee: "Fondation" should read --Foundation--.

Column 2, line 6, "$(C_{1/-C4})$" should be --$(C_1-C_4)$--.

Column 6, Table I, Ex. 14, in the column headed "product", "$(CH_1)_{11}$" should be --$(CH_2)_{11}$--.

Signed and Sealed this

Twenty-first Day of December, 1993

Attest:

BRUCE LEHMAN

*Attesting Officer*  *Commissioner of Patents and Trademarks*